United States Patent [19]

Talle et al.

[11] Patent Number: 4,731,244

[45] Date of Patent: Mar. 15, 1988

[54] MONOCLONAL ANTIBODY THERAPY

[75] Inventors: Mary A. Talle, Piscataway; Walter Newman, North Plainfield; Patricia E. Rao, Princeton Junction; Gideon Goldstein, Short Hills, all of N.J.

[73] Assignee: Ortho Pharmaceutical Corporation, Raritan, N.J.

[21] Appl. No.: 797,712

[22] Filed: Nov. 13, 1985

[51] Int. Cl.$^4$ ............................................. A61K 39/395
[52] U.S. Cl. ........................................ 424/85; 424/86; 424/87; 514/885; 935/106; 935/107; 436/548
[58] Field of Search ..................................... 424/85–87; 514/885; 935/106, 107

[56] References Cited

PUBLICATIONS

Nepon et al., *PNAS.* 81, 1984, pp. 2864–2867.
Muller et al. *J Exp. Med.* 159, 1984, pp. 758–772.
Ovary, Int. Archs Allergy Appl. Immunol. 69, 1982, pp. 385–392.
Takemori et al., Eur. J Immunol. 14, 1984, pp. 656–667.
Brown, *J Immunol.* 132, 1984, pp. 2715–2723.
Chatenoud et al., *J Immunol.* 137, 1986, pp. 830–838.
Chatenoud et al., Transplant. Proc., vol. 15, No. 1, pp. 643–645 (Mar. 1983).
Jaffers et al., Transplant Proc., vol. 15, No. 1, pp. 646–648 (Mar. 1983).

*Primary Examiner*—John Kight
*Assistant Examiner*—Garnette D. Draper
*Attorney, Agent, or Firm*—Richard J. Grochala

[57] ABSTRACT

A method of seriatim administration to a patient of a plurality of ligands, each of which contains an antigen combining site of a monoclonal antibody of distinct idiotype, is disclosed. This method is useful for therapeutic as well as diagnostic purposes.

16 Claims, 4 Drawing Figures

FIG-3

MONOCLONAL ANTIBODY THERAPY

TECHNICAL FIELD

This invention relates to monoclonal antibody therapy. More particularly, this invention relates to seriatim administration to a patient of a plurality of ligands that include the antigen combining site of a monoclonal antibody of distinct idiotype.

BACKGROUND OF THE INVENTION

Since Kohler and Milstein announced the development of hybridomas that secrete monoclonal antibodies in 1974, numerous in vitro diagnostic assays relying on the specificity of monoclonal antibodies have been comercialized. In vivo applications of monoclonal antibodies, either as therapeutic or as diagnositc agents, are less well developed, however.

Murine monoclonal antibodies are currently used therapeutically in man in a number of clinical situations, usually as immunosuppressive agents, [Cosimi et al., *New Engl. J. Med.*, 305, 308 (1981); Cosimi et al., *Transplantation*, 32,535 (1981); Chatenoud et al., *Transpl. Proc.*, 15, 643 (1983); Takahashi et al., *Lancet*, 2, 1155 (1983); and Linch et al., *Clin. Exp. Immunol*, 51, 133 (1983)] or anti-tumor agents. [Nadler et al., *Cancer Res.*, 40, 3147 (1980); Ritz et al., *Blood*, 58, 141 (1981); Miller et al., *Lancet*, 2, 226 (1981); Miller et al., *Blood*, 58, 78 (1981); Dillman et al., *Blood*, 59, 1036 (1982), Miller et al.; *New Engl. J. Med.*, 306, 517 (1982); Levy et al., *Fed. Proc.*, 42, 2652 (1983); Miller et al., *Blood*, 62, 988 (1983); and Sears et al., *Lancet*, 2, 762 (1982)]. The effect of these treatments is often initially dramatic but, as a rule, rapidly wanes because of two host escape mechanisms: antigenic modulation; i.e., the disappearance of a membrane antigen or receptor induced by binding to its specific ligand, and anti-monoclonal sensitization, the production of host antibodies against the administered monoclonal antibody.

In clinical transplantation it is a common experience that renal allograft recipients treated with conventional xenogeneic anti-lymphocyte sera (that is, sera derived from a species different from the species of the recipient) develop, within the first month of treatment, serological, and sometimes clinical, signs of xeno-sensitization against the injected foreign proteins. Attempts have been made to avoid or attenuate this sensitization by the use of monoclonal antibodies which can be administered in an effective amount at much lower doses than polyclonal antibodies. However, in most of the preliminary clinical trials using murine anti-T cell monoclonal antibodies, the patients did produce antibodies against the murine monoclonals which limited the duration of their biological effectiveness. Moreover, depending upon the treatment protocol used, the production of anti-monoclonal antibodies varied both quantitatively and qualitatively.

In particular, the murine monoclonal antibody OKT3, which is directed against mature human T cells and reacts with the T3 antigen, has been widely used since 1980 as an immunosuppressive agent to prevent or to cure rejection in renal allograft recipients. [Cosimi et al., *New Engl. J. Med.* 305, 308 (1981)].

In most instances, OKT3 was administered to treat established acute rejection episodes, while in other instances the OKT3 monoclonal antibody was administered prophylactically in order to prevent potential rejection. In an early treatment protocol, the antibody was injected alone (5 mg/day intravenously [IV]) starting on the day of transplantation and then daily for 13 consecutive days. Six patients were included in this trial. As reported in detail in Chatenoud et al., *Eur. J. Immunol.*, 12, 979 (1982), OKT produced three major immunologic effects: (1) a profound initial T cell lymphopenia, appearing within one hour following the first OKT3 injection; (2) antigenic modulation of the OKT3-defined T cell antigen; and (3) an intense xenosensitization present in five of the six treated patients.

The antigenic modulation observed in this study was not associated with the loss of OKT3-immunosuppressive activity. Indeed, in vivo modulated cells were functionally immunoincompetent. [Chatenoud et al., *id.*; Chatenoud et al., *Transplant Proc.*, 15, 643 (1983)]. However, sensitization represented a major obstacle. Specifically, as soon as significant titers of IgG anti-OKT3 antibodies appeared, the therapeutic effectiveness of OKT3 was completely abrogated. In three of the six patients entered into this protocol, significant titers were detected by Day 9 post-treatment (i.e., four days before the end of the proposed course of treatment).

Although the appearance of these anti-OKT3 antibodies was not associated with serum sickness [Jaffers et al., *Transplant. Proc.*, 15, 646 (1983)], hypersensitivity or anaphylaxis, it necessarily marked the end of the therapeutic effectiveness of the administered monoclonal antibodies.

Also, patient sensitization to the murine monoclonal antibody generally appears between Day 9 and Day 13 of antibody administration and represents an important limitation to antibody treatment.

This sensitization is heterogeneous in specificity. Some antibodies react with "mouse determinants" (anti-isotype antibodies reactive with Fc portions of the murine antibody), while the remainder are anti-idiotype antibodies (reacting with the antigen binding site variable region of the murine antibodies). [Chatenoud et al., *Transplant Proc.*, 15, 643 (1983); Jaffers et al., *Transplant. Proc.*, 15, 646 (1983)].

Once the patient is sensitized, further treatment with the monoclonal antibody is ineffective. Thus, the physician is required to continue the treatment of the patient using high dosages of conventional immunosuppressant drugs. However, these drugs have numerous adverse side effects.

It would be beneficial to be able to prolong the course of treatment using monoclonal antibodies until an allograft rejection is reversed. This would allow the physician to avoid administration of high dosage immunosuppressive drugs that must be used in the absence of monoclonal antibodies and thus the adverse effects of these drugs. The patient would have effective T cell suppression necessary for reversal of the graft rejection and none of the side effects associated with conventional immunosuppressive drugs.

In other cases where monoclonal antibody treatment is contemplated, there may be no acceptable alternative treatment. For example, surgery is an alternative method for determining the size of a tumor. However, repeated surgery is not an acceptable method for determining change in tumor size in response to therapy. In many instances the physician will not be able to closely follow the course of the disease or the patient will be without effective therapeutic treatment once the patient is sensitized to a monoclonal antibody.

SUMMARY OF THE INVENTION

The present invention contemplates a seriatim administration of a monoclonal antibody, or an antigen combining site-containing portion thereof, to a patient so as to extend the time period a patient can be effectively subjected to monoclonal antibody treatment. The present method of treatment is useful for therapeutic as well as diagnostic purposes.

The present method includes the treatment of a patient with a plurality of ligands that are administered seriatim. The ligands include antigen combining sites of monoclonal antibodies that bind to the same antigen. However, the ligands administered during each course of the seriatim administration contain distinct idiotypes.

The specific method steps are the administration for a period of time to the patient of an effective amount, usually about 10 micrograms to about 500 milligrams, of a first ligand that includes a monoclonal antibody antigen combining site of specific idiotype that binds to an antigen followed by administration to the patient, for another time period, of an effective amount of another ligand that includes a monoclonal antibody antigen combining site that is idiotypically distinct from all ligands previously administered to the patient but that is functionally equivalent to the aforementioned first ligand in binding to the same antigen.

The present method is particularly well suited for treating a patient to prevent or ameliorate an allograft rejection episode that may be acute or chronic. In that instance, the ligands contain antigen combining sites of the monoclonal antibody that bind to the T3 antigen on human T cells.

Preferred ligands useful in the allograft rejection treatment method are monoclonal antibodies OKT3, OKT3A, OKT3B, T3, LEU4, WT31, WT32 and SP34. If desired, the monoclonal antibody may be concurrently administered with an immunosuppressive drug, preferably at a dosage that is less than the dosage effective to suppress the allograft rejection in the absence of a concurrent administration of the monoclonal antibody.

Additionally, the present method of seriatim administration of monoclonal antibodies or antigen combining site-containing portions thereof can be used for therapeutic or diagnostic treatments with monoclonal antibodies for site-specific administration of cytotoxic or radiolabeled agents carried by or on monoclonal antibodies, for administration of monoclonal antibodies in the treatment of autoimmune diseases, and like applications that involve extended administration of monoclonal antibodies.

BRIEF DESCRIPTION OF THE DRAWINGS

The ordinate shows the percentage of OKT3 positive cells relative to the number of cells stained in the absence of competing monoclonal antibody as 100 percent. The abscissa shows the dilution of antibody used.

The right-most set of darkened bars illustrates the results of a cytofluorometric assay substantially similar to the assay illustrated in FIG. 1. Here, however, dilutions of the patient serum used in FIG. 2 were admixed and incubated with FITC labelled OKT8A to form admixtures. OKT8A is a murine monoclonal antibody that does not react with the T3 antigen but is of the same isotype ($IgG_{2a}$) as OKT3 antibodies. The admixtures were added to $10^6$ T cells. The ordinate shows the percentage of OKT8A positive cells relative to the number stained in the absence of competing monoclonal antibody as 100 percent. The abscissa is the same as in the remainder of the Figure.

FIG. 4 is a graph illustrating the effect of human anti-OKT3 serum on T cell mediated lympholysis blocked by monoclonal antibodies that bind to the T3 antigen on human T cells. Antibodies OKT1A and OKT11A were used as controls. $^{51}$Cr-Labelled human peripheral blood mononuclear cells from an individual (target cells) were maintained (incubated) with human peripheral blood mononuclear cells from a histoincompatible individual (responder or effector cells) in the presence of various monoclonal antibodies and human anti-OKT3 serum. The amount of T cell mediated lympholysis was determined. Briefly, cytotoxic T lymphocytes were prepared by maintaining (culturing) peripheral blood mononuclear cells from one individual (responder cells) with irradiated human peripheral blood mononuclear cells (stimulator cells) from a second histoincompatible individual at a ratio of 3:1 (responder:-stimulator). This is commonly referred to as a mixed leukocyte culture (MLC). Cells were maintained for a time period of six days at 37° C. in RPMI-1640 medium, containing 10% heat inactivated fetal calf serum and antibiotics, in a humid atmosphere containing 5% $CO_2$. On the seventh day viable cells remaining in the culture, consisting mainly of responder cells, were assayed for cytotoxicity. Briefly, peripheral blood mononuclear cells from the individual whose cells were used as stimulator cells were activated with phytohemaglutinin A (PHA), a polyclonal T cell mitogen, for a time period of 48 hours. The cells were then labelled with chromium 51 ($^{51}Cr$) to form labelled target cells. Labelled target cells (1 $\times 10^4$) were admixed and maintained (incubated) with responder cells (1 x $10^6$) (effector cells) for a time period of 4 to 6 hours at 37° C. in a humid atmosphere with 5% $CO_2$ to form cell cultures. The cell cultures were maintained in RPMI-1640 medium supplemented with 10% heat-inactivated fetal calf serum and antibiotics and containing monoclonal antibodies with or without human anti-OKT3 serum as indicated. Human anti-OKT3 serum was withdrawn from a patient who received two separate courses of OKT3 therapy following kidney transplantation as part of allograft rejection treatment. The treatment courses were approximately 22 months apart. Serum was collected 20 days after the end of the second course of OKT3 administration. The monoclonal antibodies OKT3, WT31, SP34 and WT32 were added to the culture media in the range of 35 to 75 percent inhibition. The human anti-OKT3 serum was used at a final dilution of 1:800. The monoclonal antibody OKT1A ($IgG_2$) was used at a final dilution of 1:100. OKT1A recognizes an antigen on the T cell surface distinct from the T3 antigen; it does not block T cell mediated lympholysis and was included as a negative control. The monoclonal antibody OKT11A ($IgG_2$) was added to the culture media in the range of 35 to 75 percent inhibition. OKT11A blocks T cell mediated lympholysis by binding to a T cell surface antigen distinct from the T3 antigen. After maintenance of the cell cultures for 4 to 6 hours, cells in the cultures were pelleted by centrifugation to form a cell pellet and a cell-free supernatant. 100 Microliter (ul) aliquots of the cell-free supernatant containing $^{51}Cr$ released from lysed target cells were counted in a LKB gamma counter to determine counts per minute (cpm) contained in the aliquot. The percent cytotoxicity was calculated as follows:

$$\frac{\left[\begin{array}{c}\text{cpm of assayed culture}\\ \text{supernatant}\end{array}\right] - \left[\begin{array}{c}\text{Cpm of target cell}\\ \text{culture supernatant}\end{array}\right]}{\left[\begin{array}{c}\text{total releasable cpm}\\ \text{of target cells}\end{array}\right] - \left[\begin{array}{c}\text{cpm of target cell}\\ \text{culture supernatant}\end{array}\right]} \times 100$$

The open bars indicate the percentage of cytotoxicity produced in a culture to which the indicated monoclonal antibody was added, while the striped bars indicate the percentage of cytotoxicity in a culture additionally containing human anti-OKT3 serum. The ordinate shows the percentage of cytotoxicity, while the abscissa shows the monoclonal antibody assayed.

DETAILED DESCRIPTION

Definitions

The word "allograft" as used herein and in the claims is used in its usual sense to mean a tissue or organ graft between two genetically dissimilar members of the same species.

The word "allotype" as used herein and in the claims means the genetically determined antigenic variability exhibited by different members of the same species.

The phrase "anti-idiotype antibody" as used herein and in the claims means an antibody that is specific for an antigen binding site portion of another antibody.

The phrase "anti-isotype antibody" as used herein and in the claims refers to an antibody that is specific for a constant region portion of another antibody.

The word "antigen" as used herein and in the claims denotes a molecule or a set of molecules on a cell surface, or a complex that includes such molecule or set of molecules, with which the antigen combining site of a monoclonal antibody useful for the present purposes binds.

The present method is beneficial in that it allows continued administration of a monoclonal antibody after the patient's initial development of sensitivity to a monoclonal antibody. Previously all monoclonal antibody therapy was halted once the patient was sensitized to an initially used monoclonal antibody because presently all the commercially available monoclonals are murine antibodies. It was believed that the patient's production of anti-mouse antibodies precluded effective administration of another type of murine monoclonal antibody. In renal allograft patients once these antibodies were produced the patient was treated with high dosages of immunosuppressive drugs that produce numerous adverse side effects that are not produced by the use of murine monoclonal antibodies. Moreover, treatment with OKT3 monoclonal antibody successfully reversed a greater percentage of rejection episodes than treatment with conventional immunosuppressive drugs.

As described before, the patients produce both anti-isotype and anti-idiotype antibodies in response to the monoclonal antibody. Although other murine monoclonal antibodies are commercially available that also suppress human T cells by reacting with the T-3 antigen, it was heretofore believed that the anti-mouse antibodies induced by a patient's first exposure to a murine monoclonal antibody would react with and overcome the beneficial effect of these antibodies by recognizing the isotypic portion of the antibody that the murine monoclonals antibodies all contain.

Specifically, Oi and Shulman independently described chimeric monoclonal mouse/human antibodies at the Fourth Annual Congress for Hybridoma Research in February of 1985 (*Biotechnology Newswatch*, McGraw Hill, 3-4-85, p. 2). As an attempt to solve the immunogenicity problems with mouse monoclonal antibodies, the researchers spliced human constant region portions of antibodies to murine variable region portions of antibodies to produce a human/mouse antibody since this type of antibody would be expected to be less immunogenic and therefore more effective than all mouse monoclonals. In the foregoing article Dr. Capra is reported to have stated that the efficacy of this particular approach to produce monoclonals for human use would depend on whether appropriate high secretor fusion partners ideal for all human monoclonals could be engineered.

A recent article in *Science*, 229, 455 (1985) notes that chimeric antibodies should be less antigenic than mouse monoclonal antibodies if the general supposition that the immune attack is primarily directed against the constant region of the antibodies is correct. However, if the immune response is primarily directed against the idiotype of the monoclonal antibody, the chimeric antibodies may present no advantage over mouse or other xenogeneic monoclonal antisera It has now been found that the patient's production of IgG anti-idiotype antibodies negates the effectiveness of the administered murine monoclonal antibody. Development of anti-isotype antibodies against a murine monoclonal antibody, however, does not prevent effective use of that antibody or another idiotypically distinct murine antibody. Further, the concurrent administration of a conventional immunosuppressive drug delays the production of IgG anti-idiotype antibodies produced in response to a monoclonal antibody. When a plurality of ligands including antigen combining sites containing distinct monoclonal antibody idiotypes are administered seriatim, preferably concurrently with immunosuppressive drugs at comparatively low dosages, the patient's sensitization to each monoclonal antibody idiotype can be significantly delayed, thereby extending the period of treatment by monoclonal antibodies and delaying or eliminating the need to treat the patient by a more conventional method.

For purposes of this invention, the preferred ligands are intact monoclonal antibodies having the same or different isotypes. However, the Fab or F(ab')2 portions of monoclonal antibodies can also serve as ligands, alone or in combination with another therapeutic agent.

Each ligand includes an antigen combining site of a monoclonal antibody of specific idiotype that binds to an antigen. Ligands administered seriatim after the course of treatment with a first ligand contain antigen combining sites of monoclonal antibodies that are idiotypically distinct from previously administered ligands. The ligands are functionally equivalent, however, in that each ligand binds to the same antigen.

This invention contemplates treating a patient by a seriatim administration of a plurality of ligands of this invention that each contain an antigen combining site of a monoclonal antibody. The method comprises the steps of administering to the patient for a period of time an effective amount of a first ligand and thereafter administering to the patient, for another time period, an effective amount of a ligand that is idiotypically distinct from previously administered ligands but functionally equivalent to the first ligand.

Other functionally equivalent, idiotypically distinct ligands can thereafter be administered in the same manner, if desired or deemed necessary for continued therapy.

This invention is based on the recognition that the sensitization which makes further administration of antibodies ineffective is idiotype-specific rather than isotype-specific sensitization. By changing the ligand once administration of a given ligand has become "ineffective" to a functionally equivalent ligand including an antigen combining site of a monoclonal antibody of distinct idiotype, continued, effective monoclonal antibody treatment of the patient can be prolonged.

The present invention is advantageous in that the patient can now be treated by methods that allow the continued administration of monoclonal antisera after the patient exhibits initial sensitization against a particular monoclonal antisera.

The methods of this invention are applicable to the administration of ligands containing antigen combining sites of monoclonal antibodies for either therapeutic or diagnostic purposes. The administration of a particular ligand is carried out at the same time intervals and concentrations as are generally used for the intended specific therapeutic or diagnostic purpose. For example, anti-T3 antibodies are usually given as a daily intravenous bolus of a generally used concentration to treat or prevent an allograft rejection episode.

Each ligand is administered for a period of time. This administration can be a single injection of a ligand for a diagnostic treatment, several repeated administrations of a ligand for diagnostic purposes, a continuous administration for therapeutic treatment, repeated daily injections for therapy, or like administration. The administered unit dose can be in the range of about 10 micrograms to about 500 milligrams of the ligand.

It is preferred to monitor carefully the patient during the course of treatment with each ligand to determine when anti-idiotype antibodies are produced in response to the ligand. As stated before, the treatment with a given ligand is no longer effective once anti-idiotype antibodies are produced. Preferably, the administration of another ligand is commenced at about this time.

In a preferred embodiment the present invention contemplates a method of administering seriatim to a patient a plurality of ligands containing monoclonal antibody combining sites to prevent or ameliorate an allograft rejection episode. Each ligand includes an antigen combining site of a monoclonal antibody that binds to the T3 antigen on human T cells.

For this purpose, OKT3 is an extremely effective immunosuppressant/immunomodulatory agent that has been used successfully in treating renal allograft recipients undergoing rejection or treated prophylactically immediately post-transplant to prevent rejection. OKT3 was used to treat 63 of 123 patients undergoing a first acute rejection episode after cadaveric renal transplantation in a randomized clinical trial. [Ortho Multicenter Transplant Study Group, *New Engl. J. Med.*, 313, 337 (1985)]. OKT3 used with low dosages of immunosuppressants reversed 94 percent of the rejections which was significantly better than the 75 percent reversal rate achieved with conventional high dosage steroid treatment. Further, the OKT3-treated patients had an improved one-year graft survival rate of 62 percent compared to 45 percent for the steroid-treated group.

However, the beneficial effects of this murine monoclonal antibody are later vitiated by the patients' immune response to the antibody if reversal therapy must be continued or repeated.

The present invention is based on the finding that of the two types of anti-antibodies produced against the therapeutic monoclonal antibodies, the therapeutic effectiveness of the monoclonal antibody is negated only when IgG anti-idiotype antibodies are produced. That is, high titers of either IgM anti-idiotype antibodies or IgG or IgM anti-isotype antibodies are not associated with the removal of circulating OKT3 antibodies from the bloodstream or the reappearance of immunocompetent T cells. Rather, circulating levels of OKT3 become undetectable and OKT3+T cells reappear when the patient produces IgG anti-idiotype antibodies.

Thus, only IgG and not IgM antibodies appear to be associated with loss of the therapeutic effectiveness of the administered OKT3. Second, only anti-idiotype but not anti-isotype antibodies were associated with loss of therapeutic effectiveness of administered OKT3. Third, the addition of low-dosage corticosteroids and azathioprine, but not corticosteroids alone, significantly reduced anti-monoclonal immunization both qualitatively and quantitatively. That is, the appearance of anti-monoclonal antibodies was not observed in some patients, and the kinetics of appearance of anti-monoclonal antibodies were delayed significantly in the remaining patients in comparison to patients treated with OKT3 alone.

Therefore, the monoclonal sensitization obstacle to the use of monoclonal antibodies to treat allograft rejection is overcome by administering seriatim to the sensitized patient other ligands containing antigen combining sites of other monoclonal antibodies of distinct idiotypes that function substantially in a like manner in binding to the T3 antigen of human T cells. The sensitization obstacle can be further delayed using relatively low-dosages of conventional immunosuppressive drugs concurrently with administration of the monoclonal antibody.

Table I, below, describes additional preferred ligands including idiotypically distinct anti-T3 monoclonal antibody combining sites useful in an exemplary therapeutic method of the present invention for treatment of allograft rejection episodes. While it is preferred to administer these ligands as intact monoclonal antibodies, the Fab or F(ab')2 portions thereof are also suitable.

TABLE I

MONOCLONAL ANTIBODY TYPES REACTIVE WITH THE T3 ANTIGEN ON HUMAN T CELLS

| Monoclonal Ab | Source | Ig Isotype | ATCC No. |
|---|---|---|---|
| OKT3 | Immunobiology Division Ortho Pharmaceutical Corp. | $IgG_{2a}$ | CRL 8001 (4/26/79)[3] |
| OKT3A | Immunobiology Division Ortho Pharmaceutical Corp. | $IgG_{2a}$ | HB 8907 (9/26/85) |
| OKT3B | Immunobiology Division Ortho Pharmaceutical Corp. | $IgG_{2a}$ | HB 8908 (9/26/85) |
| T3 | Coulter Diagnostics | $IgG_1$ | |
| LEU4 | Becton-Dickinson | $IgG_1$ | |
| WT31[1] | | $IgG_1$ | |
| WT32[1] | | $IgG_2$ | |
| Sp34[2] | | $IgG_3$ | |

[1]These antibodies are described in Tax et al., Nature, 304, 445 (1983). WT31 is reactive with the constant portion of the antigen recognition structure of human T cells which is closely associated with T3.
[2]This antibody is described in Pessano et al., EMBO J., 4, 337 (1985).
[3]Date of deposit with ATCC.

The allograft treatment method comprises the following steps. An effective amount of a ligand including an antigen combining site of a monoclonal antibody that binds to the T3 antigen on human T cells is administered to the patient for a period of time. Thereafter an effective amount of another ligand that includes an antigen combining site of another monoclonal that binds to the T3 antigen but is idiotypically distinct from previously administered ligands is administered to the patient. This administration commences at a time not later than upon detection of anti-idotypic antibodies to the immediately preceeding ligand.

The seriatim administration of idiotypically distinct ligands including monoclonal antibody anti-T3 combining sites may be repeated when anti-idiotype antibodies are detected as aforedescribed.

For treatment of allograft rejections, an intact monoclonal antibody is preferably administered intravenously (IV) in a dosage of about 1 to about 10 milligrams (mg) per day. Most preferred is a daily IV bolus of about 5 mg.

Preferably, each patient is carefully monitored to determine when anti-idiotype antibodies are produced in response to the administration of the ligand. The treatment with the ligand can thereby be extended for a maximum practical time period. However, such monitoring may not be always available. Inasmuch as it would be detrimental to the patient to allow immunocompetent T cells to reappear before the rejection episode was terminated, a study was undertaken to determine standard, appropriate administration times for monoclonal antibodies or Fab or F(ab')2 portions thereof. A ligand containing a T3 reactive antigen combining site of a monoclonal antibody is preferably administered for about 10 to about 28 days. A most preferred administration regimen is about 10 to about 14 days for each monoclonal antibody.

Each monoclonal antibody may also preferably be administered concurrently with conventional immunosuppressive drugs, as described before. Conventional immunosuppressive drugs include alkylating agents such as chlorambucil; corticosteroids such as hydrocortisone, methylprednisolone, and prednisone; antimetabolites such as cytosine arabinoside, aminopterin, amethopterin, 6-mercaptopurine, cyclophosphamide, and azathiopurine; and antibiotics, such as cyclosporine.

When an immunosuppressive drug is concurrently administered with a T3-reactive monoclonal antibody, it is preferably administered in a dosage that is less than the dosage of the drug effective to suppress the allograft rejection in the absence of a concurrent monoclonal antibody administration. In this way the adverse effects of conventional immunosuppressants are minimized and the time period required to sensitize the patient to the monoclonal antibody type is extended.

Figure 1:
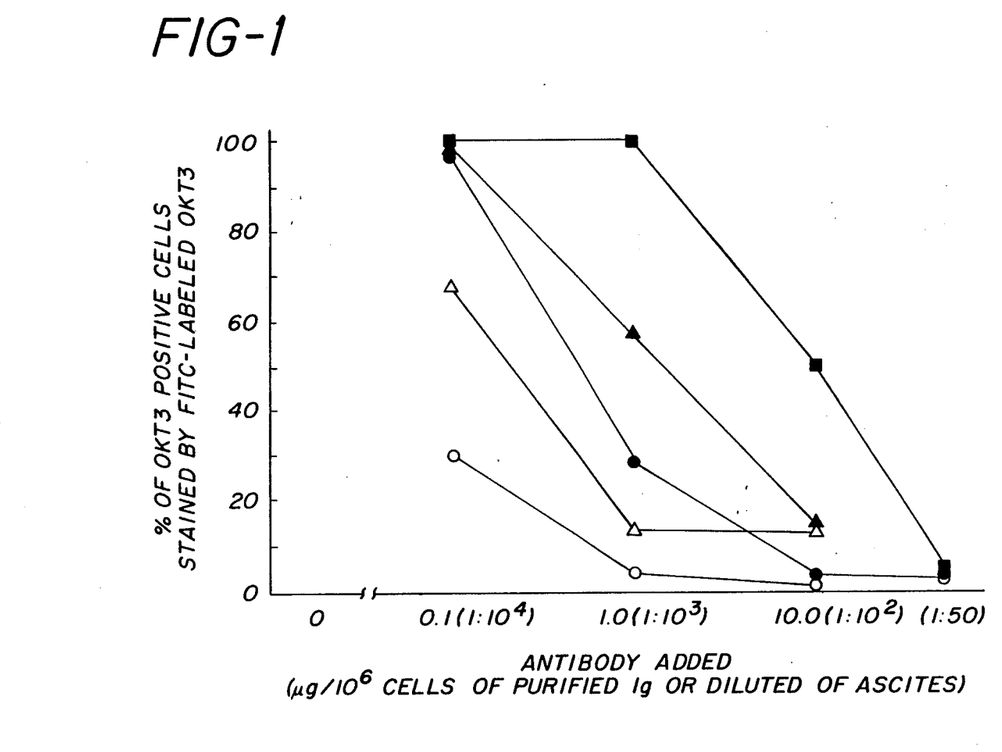
FIG. 1 is a graph illustrating the results of cytofluorometric analysis of inhibition of binding of fluorescein isothiocyanate-labelled OKT3 antibodies (FITC-OKT3) to human T cells by the indicated dilutions of monoclonal antibodies. The monoclonal antibodies used are WT32 ascites [darkened squares (■)], LEU4 [darkened triangles (▲)], T3 [open triangles (Δ)], WT31 ascites [darkened circles(●)], and OKT3 ascites [open circles (○)]. A predetermined subsaturating amount of FITC-OKT3 was admixed with dilutions of the indicated monoclonal antibodies to form an admixture. $10^6$ T cells were added to the admixture to form a second admixture that was maintained (incubated) at 4° C. for 30 minutes. Cells in the second admixture were then washed to remove unbound FITC-OKT3 prior to immunofluorescence analysis using a Cytoflurograf (Ortho Diagnostic Systems, Inc., Raritan, NJ).

As illustrated in FIG. 1, monoclonal antibodies T3, LEU4, WT31 and WT32 all bind to the T3 antigen on human T cells and thereby block binding of OKT3 antibodies to the T3 antigen. These antibodies bind to the same antigen as OKT3 and thereby produce substantially similar patterns of immunosuppression as OKT3 antibodies.

Figure 2:
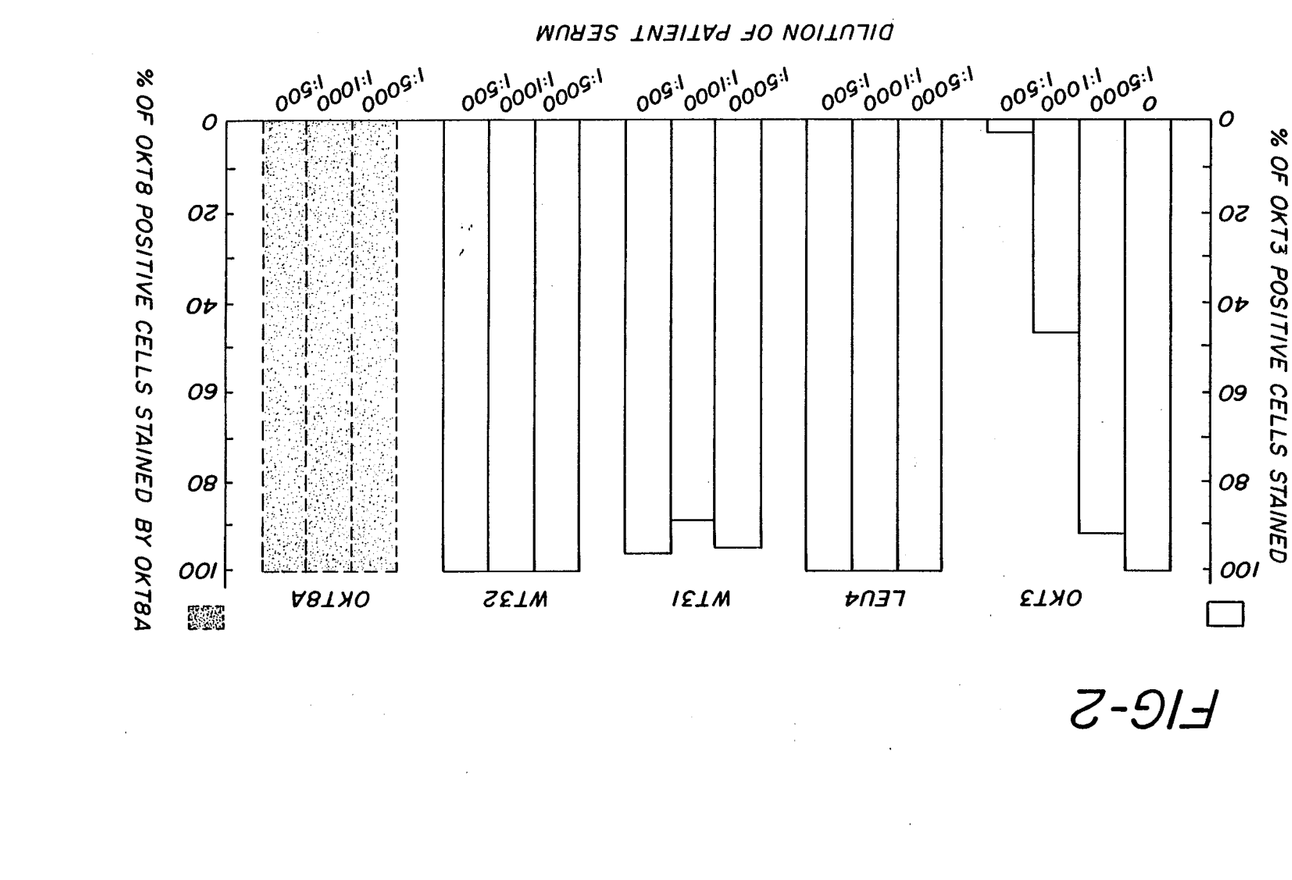
FIG. 2 is a graph in which the left-most four sets of bars illustrate lack of inhibition of binding of T3-reactive monoclonal antibodies to OKT3 positive cells by dilutions of serum from a patient treated with OKT3. The serum was determined to contain anti-OKT3 antibodies and no OKT3 antibodies by enzyme-linked immunosorbent assay (ELISA) Predetermined subsaturating amounts of the indicated types of murine monoclonal antibodies that bind to the T3 antigen on human T cells were admixed with the indicated dilutions of patient serum to form admixtures. The admixtures were maintained (incubated) for a time period of 20 minutes at room temperature (about 25° C.) Thereafter $10^6$ T cells were added to each admixture to form a second admixture. The second admixtures were maintained for 30 minutes at 4° C. Thereafter the cells of each of the second admixtures were washed to remove unbound antibody. Detection of antibody bound to the cells was accomplished by admixing and maintaining the cells with FITC-labelled goat anti-mouse immunoglobulin reagent (TAGO, Inc., Burlingame, Ca.) in a manner similar to that described in FIG. 1. Immunofluorescence was determined using an Ortho Cytofluorograf. The ordinate shows the percentage of OKT3 positive cells relative to the number of cells stained in the absence of competing monoclonal antibody as 100 percent. The abscissa shows the dilution of patient serum.

However, as illustrated in FIG. 2, anti-OKT3 antibodies induced in patients undergoing OKT3 antibody treatment do not block the binding of idiotypically distinct T3 reactive murine monoclonal antibodies. Therefore, patient antibodies induced by administration of OKT3 antibodies that render further treatment with OKT3 antibodies ineffective do not interfere with an effective treatment with other idiotypically distinct murine T3 reactive antibodies.

The allograft rejection treatment method of this invention provides to the patient a ligand including a T3 reactive antigen combining site of a monoclonal antibody while each ligand is still effective as an immunosuppressant and then supplies to the patient another ligand including another idiotypically distinct T3 reactive antigen combining site of a monoclonal antibody. This seriatim administration of ligands including an antigen combining site of a monoclonal antibody, for no longer than the time period until the patient produces anti-idiotype antibodies that render further treatment with the ligand ineffective, can extend the period of time during which the patient can be effectively treated with monoclonal antibodies.

Moreover, a patient sensitized to one murine monoclonal antibody idiotype in a prior rejection treatment episode can be effectively treated with another idiotypically distinct murine monoclonal antibody, or with several idiotypically distinct antibodies administered one after another during a subsequent rejection episode.

Figure 3:
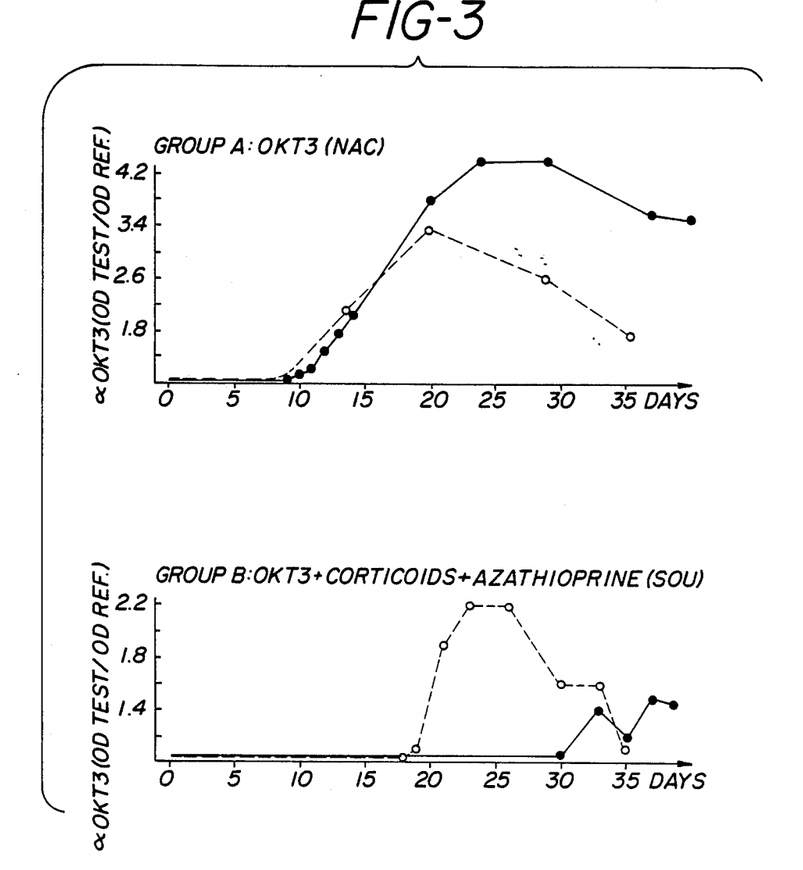
FIG. 3 consists of two graphs illustrating ELISA-determined serum IgM and IgG anti-OKT3 antibody values produced in a representative renal allograft patient from each of two groups. Group A patients received 5 mg of OKT3 per day intravenously beginning the day of transplantation. Group B patients additionally received 3 mg/kg/day of azathiopurine and 0.25 mg/kg/day of prednisone. The open circles and broken lines indicate IgM values while the closed circles and lines indicate IgG values. The ordinates show the difference in optical density between test and reference values in the ELISA assay. The abscissas show the day the serum was drawn with "0" indicating the day of transplantation.

FIG. 3 illustrates the results of a study of two groups of patients who underwent two different types of treatment regimens. Group A patients were administered an exemplary ligand containing a T3 reactive monoclonal antibody idiotype (OKT3) alone, while Group B patients were administered the same dosage of the antibody concurrently with conventional immunosuppressive drugs at reduced dosages. FIG. 3 shows the IgG and IgM anti-OKT3 antibody levels produced by a representative patient in each group. As can be seen in this Figure, patients receiving the monoclonal antibody alone begin to produce significant IgG and IgM anti-OKT3 antibody levels at about Day 10. However, Group B patients produce IgM antibody around Day 18 and begin to produce IgG antibodies around Day 30.

The study involved seven patients in Group A who received 5 mg of OKT3 per day injected intravenously (IV) as a bolus beginning on the day of renal transplantation and continuing for a total of fourteen consecutive days. Group B comprised eleven patients who received the same daily bolus of OKT3 as Group A patients and additionally received 3 mg/kilogram (kg) per day (mg/kg)/day) of azathioprine and 0.25 mg/kg/day of prednisone for fourteen to thirty days. The representative patient (SOU) used in the FIG. received treatment through day 30. The patient's IgG and IgM anti-OKT3 serum antibody titers were determined by enzyme-linked immunosorbant assay (ELISA).

Briefly, ELISA microplates were coated with OKT3 at a concentration of 0.2 micrograms (ug) per microwell. The fixation of human IgM or IgG anti-OKT3 antibodies was detected in parallel using standard protocols for horseradish peroxidase-labeled goat anti-human IgM and IgG (Institut Pasteur Production, France), respectively.

As determined in this study, patients became sensitized as early as Day 10 in the absence of concurrently administered conventional immunosuppressive drugs. The patients additionally receiving such immunosuppressants can be treated for 28 days or more before sensitization limits the effectiveness of the monoclonal antibody treatment.

Figure 4:
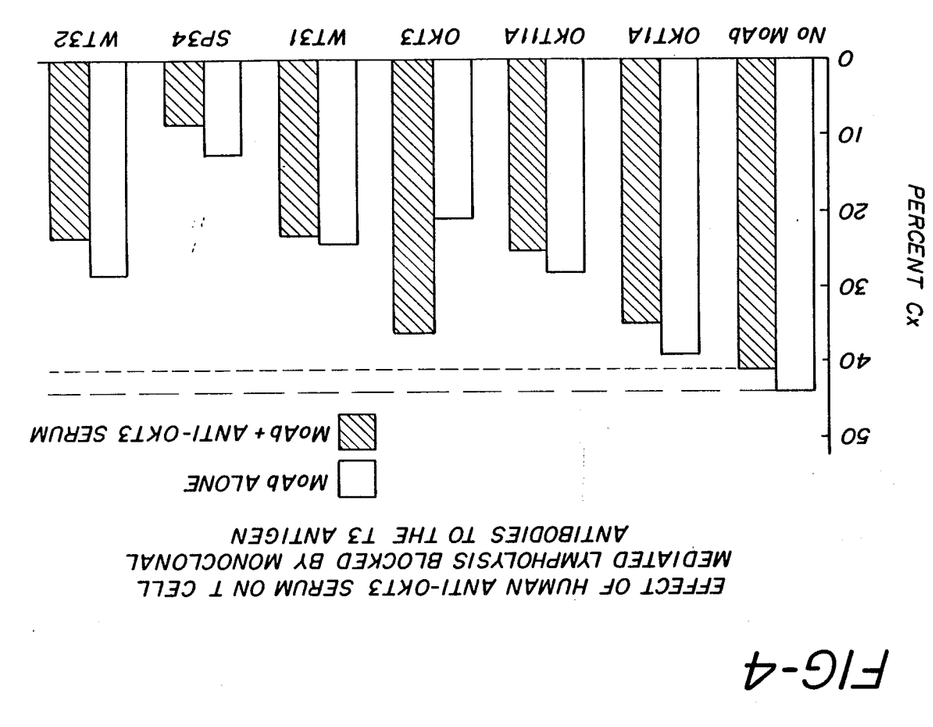

FIG. 4 illustrates the effect of human anti-OKT3 serum on T cell mediated lympholysis (CML) blocked by monoclonal antibodies reactive with the T3 antigen. Cytoxic T cells were prepared using a mixed leukocyte culture (MLC). MLC is regarded as the in vitro counterpart of allograft rejection in vivo. [Costa et al., Science, 229, 176 (1985)]. These cells were admixed with labelled target cells in the presence of various ligands including antigen combining sites of monoclonal antibodies that bind to the T3 antigen present in the culture medium at inhibitory concentrations with and without added human anti-OKT3 serum. OKT11A, an IgG$_{2a}$ murine monoclonal antibody reactive with cell surface protein distinct from the T3 antigen, was used as a control.

As shown in the Figure, human anti-OKT3 inhibited the ability of OKT3 to block cytolysis but did not inhibit the ability of the other T3 reactive monoclonal antibodies to block cytolysis. The addition of anti-OKT3 serum to monoclonal OKT 11A did not alter the assay result.

The assays illustrated in FIG. 4 demonstrate that the anti-T3 monoclonal antibodies assayed inhibit cell lysis in comparison to a cell culture without added monoclonal antibody. The inhibition of cell lysis produced by OKT3 is substantially blocked by the presence of anti-OKT3 serum in the culture. However, the anti-OKT3 serum has no significant effect on the inhibition of lysis produced by the other T3 reactive monoclonal ligands.

The present method of seriatim administration of monoclonal antibodies or antigen combining site portions thereof can also be used for therapeutic or diagnostic treatment with monoclonal antibodies for site-specific administration of cytotoxic or radiolabeled agents. Other preferred ligands are administered for treatment of autoimmune diseases and like applications that involve extended administration of monoclonal antibodies.

Ultrasound, computerized tomography, and the like radiological noninvasive imaging techniques have reduced the need for exploratory surgery. Monoclonal antibodies coupled to imaging agents such as contrast enhancing dyes or radioactive isotypes can be used to bind to target tissues.

For example, a monoclonal antibody that reacts with a protein found inside cardiac muscle cells has been developed. When cells are killed during a heart attack, the protein is exposed. Radiolabeled monoclonal antibody is injected into the patient's bloodstream, specifically binds to and accumulates in areas of the heart containing dead and damaged cells, and is imaged by a gamma ray camera. This technique has been tested and reportedly will be clinically available in the near future. (Rex Chisholm, *High Technology*, Jan 1983, 57).

Monoclonal antibodies specific for tumor cell surface antigens can be used in a similar manner to detect tumors, define a tumor's size, or monitor changes in tumor size during treatment.

Further, monoclonal antibodies are undergoing clinical testing in several institutions as therapeutic agents. Regression of tumors in patients with advanced cases of malignant melanoma using a murine monoclonal antibody that has inherent cytotoxic activity has been reported. (*Biotechnology Newswatch*, McGraw-Hill, 6-17-85, p. 1).

Although some monoclonal antibodies are cytotoxic when administered alone, other monoclonal antibodies are not. The latter types of monoclonal antibodies can be coupled to cytotoxic agents that will be brought into contact with the target tissue by the monoclonal antibody. For example, radioimmunotherapy in which radioisotopes such as iodine 131 are coupled to conventional antibodies such as those directed against liver tumor-associated antigens has been developed. (*High Technology*, Jan. 1983, 57).

Monoclonal antibodies directed against such antigens can be coupled to radioisotopes or other cytotoxic agents such as methotrexate, vinblastine or other drugs conventionally used to treat cancer. In this way the drug is deposited in a specific area of the body and thereby the side effects of generalized administration of these agents are reduced. The aforedescribed technique can be further refined using monoclonal antisera with its improved specificity in comparison to polyclonal antisera.

Further, monoclonal antibodies are also contemplated for use in treating autoimmune diseases by binding to the autoimmune antibody. These monoclonal antibodies can also regulate autoimmune diseases by binding and killing lymphocytes that produce undesired autoimmune reactions in a manner similar to a method for treating allograft rejections. Similar procedures may be used to kill lymphocytes producing IgG antibodies that cause allergic responses. (id.).

These or other treatments that involve the extended or repeated administration of monoclonal antibodies are clinical situations in which the method of this invention is beneficial. Each ligand including an antigen combining site of a monoclonal antibody whether administered alone or coupled to another therapeutic or diagnostic agent is administered to the patient while the ligand is still effective; that is, until anti-idiotype antibodies to the immediately preceding ligand are detected. Thereafter, the patient is treated with an idiotypically distinct but functionally equivalent ligand.

The foregoing is intended as illustrative of the present invention but is not limiting. Numerous variations and modifications can be effected without departing from the spirit and scope of the novel concepts of the invention. It is to be understood that no limitations with respect to the specific antibodies, compositions and uses described herein is intended or should be inferred.

We claim:

1. A method for prolonging the time period a patient can be effectively subjected to therapeutic monoclonal antibody treatment, comprising:
   (a) administering to said patient an effective amount of a first monoclonal antibody, or an antigen binding fragment thereof, until the patient produces a detectable amount of an anti-idiotype antibody against said first antibody or fragment thereof; and
   (b) thereafter administering to said patient an effective amount of a second monoclonal antibody, or an antigen binding fragment thereof, wherein said second antibody or fragment is idiotypically distinct from said first antibody or fragment but functionally equivalent to said first antibody or fragment in binding to the same antigen.

2. The method of claim 1 wherein step (b) is repeated.

3. The method of claim 1 wherein said monoclonal antibodies have the same isotype.

4. The method of claim 1 wherein said monoclonal antibodies have different isotypes.

5. The method of claim 1 wherein at least one of said fragments is selected from the group consisting of a Fab and F (ab')$_2$ portions of monoclonal antibodies.

6. A method for treating or ameliorating an acute or chronic allograft rejection episode in a patient. comprising:
   (a) administering to said patient a first monoclonal antibody, or an antigen binding fragment thereof, which includes an antigen binding site for the T3 antigen on human T cells in an amount effective to prevent or amieliorate an allograft rejection episode, said administration continuing unitl the patient produces a detectable amount of an anti-idiotype antobody against said first antibody or fragment thereof; and
   (b) thereafter administering to said patient an effective amount of a second monoclonal antibody, or an antigen binding fragment thereof, which includes an antigen binding site for the T3 antigen on human T cells, but is idiotypically distinct from said first antibody fragment.

7. The method of claim 6 wherein step (b) is repeated.

8. The method according to claim 6 wherein one of said fragments is selected from the group consisting of Fab and F (ab')$_2$ portions of monoclonal antibodies.

9. The method according to claim 6 wherein said first or second monoclonal antibodies are selected from the group of monoclonal antibodies consisting of OKT3, OKT3A, OKT3B, T3, LEU4, WT3I, WT32, and SF34.

10. The method according to claim 6 wherein said monoclonal antibodies or fragments are adminstered intravenously in a dosage of about 1 milligram to about 10 milligrams per day.

11. The method according to claim 6 wherein said monoclonal antibodies or fragments are administered intravenously in a dosage of about 5 milligrams per day.

12. The method according to claim 6 wherein each antibody or fragment is adminstered to the patient for a time period of about ten to about twenty eight days.

13. The method according to claim 6 wherein each antibody or fragment is administered to the patient for a time period of about ten to about fourteen days.

14. The method according to claim 6 wherein an immunosuppressive drug is administered concurrently with said administration of the antibody or fragment.

15. The method according to claim 14 wherein said immunosuppressive drug is administered in a dosage that is less than the dosage of said drug effective to suppress the allograft rejection in the absence of a concurrent administration of a monoclonal antibody.

16. The method according to claim 14 wherein said immunosuppressive drug is selected from a drug that is a member of the group consisting of an alkylating agent, a corticosteroid, an antimetabolite, and an antibiotic.

* * * * *

UNITED STATES PATENT AND TRADEMARK OFFICE
CERTIFICATE OF CORRECTION

PATENT NO. : 4,731,244

DATED : March 15, 1988

INVENTOR(S) : Mary Anne Talle et al

It is certified that error appears in the above-identified patent and that said Letters Patent is hereby corrected as shown below:

Claim 6, column 14, line 8: "amieliorate" should be --ameliorate --.

Claim 6, column 14, line 11: "antobody" should be --antibody--.

Signed and Sealed this

Eleventh Day of July, 1989

Attest:

DONALD J. QUIGG

Attesting Officer

Commissioner of Patents and Trademarks